US008426857B2

(12) United States Patent
Kamikubo

(10) Patent No.: US 8,426,857 B2
(45) Date of Patent: Apr. 23, 2013

(54) SEMICONDUCTOR DEVICE AND METHOD FOR PRODUCING THE SAME

(75) Inventor: Noritaka Kamikubo, Osaka (JP)

(73) Assignee: Sharp Kabushiki Kaisha, Osaka (JP)

( * ) Notice: Subject to any disclaimer, the term of this patent is extended or adjusted under 35 U.S.C. 154(b) by 0 days.

(21) Appl. No.: 12/994,377

(22) PCT Filed: May 11, 2009

(86) PCT No.: PCT/JP2009/058774
§ 371 (c)(1),
(2), (4) Date: Feb. 7, 2011

(87) PCT Pub. No.: WO2009/142121
PCT Pub. Date: Nov. 26, 2009

(65) Prior Publication Data
US 2011/0114951 A1  May 19, 2011

(30) Foreign Application Priority Data

May 23, 2008 (JP) ................................. 2008-135459

(51) Int. Cl.
*H01L 21/66* (2006.01)
(52) U.S. Cl.
USPC ............... 257/48; 257/E23.179; 257/E21.53; 438/16; 702/153; 702/159; 702/166; 702/167; 382/151; 356/401; 356/503; 356/516
(58) Field of Classification Search ............ 257/48, 257/E23.179, E21.529, E21.53; 702/117, 702/150–153, 155, 158, 159, 166, 167; 356/237.4, 356/237.5, 401, 503, 516; 382/145, 151; 438/16
See application file for complete search history.

(56) References Cited

U.S. PATENT DOCUMENTS

| 4,757,207 | A | * | 7/1988 | Chappelow et al. | ....... 250/491.1 |
| 5,214,489 | A | * | 5/1993 | Mizutani et al. | .............. 356/490 |
| 5,293,216 | A | | 3/1994 | Moslehi | |

(Continued)

FOREIGN PATENT DOCUMENTS

| JP | 63-019830 | 1/1988 |
| JP | 01-232736 | 9/1989 |

(Continued)

OTHER PUBLICATIONS

International Search Report for PCT/JP2008/058774, mailed Aug. 11, 2009.

*Primary Examiner* — Fernando L Toledo
*Assistant Examiner* — Victoria K Hall
(74) *Attorney, Agent, or Firm* — Nixon & Vanderhye P.C.

(57) ABSTRACT

A method for producing a semiconductor device comprising a process step of forming a device configuration pattern in a device formation region in a chip formation region on a film side of a semiconductor wafer having the film for forming a pattern, and forming inspection patterns in a plurality of inspection regions in the chip formation region, and an inspection step, wherein the inspection patterns have a repeat pattern and a uniform pattern formed in a first inspection region in the plurality of inspection regions, the inspection step has at least a pattern inspection step including a first inspection to measure a parameter of the repeat pattern, by using an optical measurement method capable of measuring a three-dimensional pattern shape, and a second inspection to measure a film thickness of the uniform pattern by using an optical measurement method capable of measuring the film thickness.

21 Claims, 7 Drawing Sheets

U.S. PATENT DOCUMENTS

| | | | |
|---|---|---|---|
| 5,528,372 A * | 6/1996 | Kawashima | 356/401 |
| 5,579,207 A * | 11/1996 | Hayden et al. | 361/790 |
| 5,867,276 A | 2/1999 | McNeil et al. | |
| 6,891,626 B2 * | 5/2005 | Niu et al. | 356/625 |
| 6,963,389 B2 * | 11/2005 | Fukada | 355/53 |
| 7,197,737 B1 * | 3/2007 | Iandolo et al. | 716/124 |
| 7,241,538 B2 * | 7/2007 | Zhang et al. | 430/5 |
| 7,643,140 B2 * | 1/2010 | Ueno et al. | 356/237.4 |
| 7,676,078 B2 * | 3/2010 | Fukuhara | 382/147 |
| 7,783,669 B2 * | 8/2010 | Qiu et al. | 707/793 |
| 7,821,638 B2 * | 10/2010 | Kim | 356/401 |
| 2001/0010271 A1 * | 8/2001 | Lin et al. | 174/255 |
| 2005/0277035 A1 * | 12/2005 | Yamamoto | 430/30 |
| 2006/0244969 A1 * | 11/2006 | Ryan et al. | 356/446 |
| 2009/0214103 A1 * | 8/2009 | Tanaka et al. | 382/145 |

FOREIGN PATENT DOCUMENTS

| | | | |
|---|---|---|---|
| JP | H01-232736 | * | 9/1989 |
| JP | 2003-294436 | | 10/2003 |
| JP | 2003-344029 | | 12/2003 |
| JP | 2004-158478 | | 6/2004 |
| JP | 2004-207353 A | | 7/2004 |
| JP | 2004-219343 | | 8/2004 |
| JP | 2006-100619 | | 4/2006 |
| JP | 2006-112884 | | 4/2006 |
| JP | 2006-337374 | | 12/2006 |
| JP | 2007-281384 | | 10/2007 |

* cited by examiner

SEMICONDUCTOR DEVICE AND METHOD FOR PRODUCING THE SAME

This application is the U.S. national phase of International Application No. PCT/JP2009/058774, filed 11 May 2009, which designated the U.S. and claims priority to Japanese Patent Application No. 2008-135459, filed 23 May 2008, the entire contents of each of which are hereby incorporated by reference.

TECHNICAL FIELD

The technology presented herein relates to a semiconductor device and a method for producing the same and more particularly, to a semiconductor device structure in which a shape dimension of a pattern to be formed can be improved in management and measurement accuracy, and a method for producing the same.

BACKGROUND ART AND SUMMARY

With the increase in integration of a semiconductor device, a pattern formed in a production process of the semiconductor device is miniaturized, and a shape dimension of the pattern is required to be managed and measured with high accuracy.

Representative means for measuring the shape dimension of the pattern includes a spectroscopic ellipsometry method using visible light or UV light, a critical dimension secondary electron microscope (CD-SEM) method using an electron beam, and the like.

The spectroscopic ellipsometry method is used to measure a shape dimension in a vertical direction with respect to a wafer surface such as a film thickness of a deposited film or a process film. Meanwhile, the CD-SEM method is used to measure a shape dimension in a horizontal direction with respect to the wafer surface such as a process line width or critical dimension (CD).

In the case of a measurement of a film thickness of a film which is not likely to transmit the visible light and UV light such as a trench process shape to form a STI (Shallow Trench Isolation) structure, a transistor shape and a wiring film thickness, and a measurement of a shape dimension having a three-dimensional structure, it is hard to measure them with high accuracy by the spectroscopic ellipsometry method or the CD-SEM method. For example, as shown in FIG. 7, in the case of a measurement of a third-dimensional shape in which a silicon oxide film 902, and a silicon nitride film 903 are sequentially formed on a semiconductor substrate 901, and a trench 904 to be filled with an insulation film is formed in the STI region, a high-accuracy measurement cannot be made by the spectroscopic ellipsometry method or the CD-SEM method.

Thus, an atomic force microscope (AFM) method, or a cross section secondary electron microscope (X-SEM) method is used when such a three-dimensional shape is measured.

However, these methods are low in throughput and performed through a contact or destructive inspection, so that cost required for a management of a production process problematically increases.

One of the means to solve the problem includes a scatterometry method (light-wave scattering measurement method) using a light wave. For example, Patent Document 1 discloses a principle to measure a shape dimension of a pattern by the scatterometry method. In addition, Patent Document 2 discloses a method to measure a shape dimension of a surface of a semiconductor device.

According to the scatterometry method, a repeat pattern provided with lines and spaces alternately is irradiated with a measurement beam, and shape dependency characteristics of the repeat pattern of reflected light in a light wavelength band are calculated by numerical analysis, and a three-dimensional shape of the pattern is found by comparing it with an actual measurement value.

Specifically, the scatterometry method uses the fact that when a measurement beam is obliquely applied to a surface of a semiconductor wafer, and the measurement beams are applied from various angles with respect to an angle $\alpha$ which is an in-plane rotation direction containing the wafer surface, spectrums of reflected and diffracted light change according to the three-dimensional pattern shape of the surface of the semiconductor wafer (see FIG. 8).

In this case, theoretical spectrums for a plurality of model pattern shapes are simulated and put in a library management. Thus, by comparing it with actual spectrum obtained from the surface of the semiconductor wafer, that is, by performing fitting, a three-dimensional shape of the closest model pattern is extracted as a measurement value.

With this method, the wafer can be measured in a nondestructive and non-contact manner under air pressure with a high throughput.

For example, in the case of the pattern shape shown in FIGS. 7 and 8, parameters which determine the three-dimensional shape include a pattern line width (CD1) 911, a space line width (CD2) 912, a substrate trench depth 921, a silicon oxide film thickness 922, a silicon nitride film thickness 923, and a tapered angle 931.

When the three-dimensional shape is measured by the scatterometry method, an inspection region 941 having a repeat pattern having identical line widths and identical space widths as shown in FIG. 8 is laid out on the semiconductor wafer, the inspection region 941 is irradiated with a measurement beam (white incident light) 951 at an incident angle of $\theta$, and spectrums of reflected and diffracted light 952 are obtained with respect to a plurality of angles $\alpha$. Thus, by fitting the obtained measurement result to the three-dimensional shape of the model pattern, the parameters 911, 912, 921 to 923, and 931 are determined at the same time, and these values are set to the measurement values of the three-dimensional shape.

Meanwhile, the three-dimensional shape to be measured in the surface of the semiconductor wafer is not completely unpredictable, and actually it is limited to some extent with respect to each production process.

Therefore, Patent Document 3, for example discloses a method to facilitate the fitting performed when a resist shape is measured by previously simulating an assumed change of the resist shape as a model pattern and putting in a library management, with respect to fluctuation of a process parameter which is predicted in a lithography step.

In addition, Patent Document 4 improves fitting validity by previously creating a test sample having fluctuated parameters which are predicted in a production step, and putting spectrum data obtained from the test sample and three-dimensional shape data obtained by measuring the test sample according to another method (such as AFM method) in a library management.

Furthermore, Patent Document 5 discloses a method to measure a three-dimensional shape using both of the AFM method and the scatterometry method, and Patent Document 6 discloses a method to obtain height information of a pattern by the scatterometry method and to measure a three-dimensional shape using the height information by the CD-SEM method.

PRIOR ART DOCUMENTS

Patent Documents

Patent Document 1: U.S. Pat. No. 5,293,216
Patent Document 2: U.S. Pat. No. 5,867,276
Patent Document 3: Japanese Patent Application Laid-Open No. 2003-344029
Patent Document 4: Japanese Patent Application Laid-Open No. 2004-158478
Patent Document 5: Japanese Patent Application Laid-Open No. 2003-294436
Patent Document 6: Japanese Patent Application Laid-Open No. 2004-219343

As described above, the scatterometry method is an optical method which can be implemented in a nondestructive and non-contact manner with a high throughput, and can theoretically measure a plurality of parameters to determine the three-dimensional shape by sufficiently enhancing spectroscopic accuracy.

However, it is necessary to collect a large amount of model patterns in which parameter values are fluctuated, and the model pattern data contains many fitting parameters. Therefore, an enormous amount of fitting calculations is needed to determine which model pattern data of the large amount of model pattern data is the closest to the three-dimensional data obtained by actually measuring a target measurement object, so that a high-accuracy measurement value cannot be obtained in a short time.

In addition, according to the method disclosed in Patent Documents 3 and 4, although a fluctuation range of each fitting parameter can be limited, the parameter number is not changed (not reduced), so that a fitting calculation having large degree of freedom is also needed. That is, since many fitting parameters are contained in the model pattern data, the fitting calculation becomes enormous.

In addition, according to the method disclosed in Patent Documents 5 and 6, although the parameter number can be reduced, the measurement by the AFM or CD-SEM is needed, so that its throughput is reduced, and it is difficult to measure all of the samples in a production process of a mass product. Therefore, a small number of wafers are sampled in each lot and a representative measurement value from them is used, so that it is appropriate for management of a lot unit, but it is difficult to obtain a high-accuracy measurement value of the three-dimensional shape with respect to each wafer to manage the shape of each wafer in a short time.

That is, since at least one of the plurality of parameters for measurement of the three-dimensional shape by the scatterometry method is measured by the AFM or CD-SEM method, the fitting parameter number can be reduced and the measurement accuracy can be improved by the scatterometry method, but a process ability is small because the AFM or CD-SEM method is used together.

The technology presented herein was made to solve the above problems and provides a semiconductor device whose three-dimensional shape of a pattern can be measured in a nondestructive and non-contact manner under air pressure with a high throughput and high accuracy, and whose shape dimension can be managed with high accuracy, and a method for producing the same.

Therefore, the technology presented herein provides a method for producing a semiconductor device including a process step of forming a device configuration pattern in a device formation region in a chip formation region on a film side of a semiconductor wafer having the film for forming a pattern, and forming inspection patterns in a plurality of inspection regions in the chip formation region, and an inspection step, wherein the inspection patterns have a repeat pattern having identical lines and identical spaces formed in a first inspection region in the plurality of inspection regions, and a uniform pattern having no space, formed in a second inspection region in the plurality of inspection regions, the inspection step has at least a pattern inspection step including a first inspection to measure a parameter of the repeat pattern alternately provided with the line and space in a repeat direction in the first inspection region, by using an optical measurement method capable of measuring a three-dimensional pattern shape, and a second inspection to measure a film thickness of the uniform pattern in the second inspection region by using an optical measurement method capable of measuring the film thickness.

Note that, the device configuration pattern and the inspection pattern are formed, based on predetermined layout data, as a matter of course.

In addition, according to another aspect of the technology presented herein, there is provided a semiconductor device having a device configuration pattern composed of a film for forming a pattern, formed in a device formation region, and inspection patterns composed of the film for forming the pattern, formed in a plurality of inspection regions, on a surface of a semiconductor chip, in which the inspection patterns have a repeat pattern having identical lines and identical spaces formed in a first inspection region of the plurality of inspection regions, and a uniform pattern having no space, formed in a second inspection region of the plurality of inspection regions.

According to a method for producing a semiconductor device of the technology presented herein, a parameter (two-dimensional shape) of an inspection repeat pattern in a repeat direction is measured in a first inspection by an optical measurement method capable of measuring a three-dimensional pattern shape, and a parameter (one-dimensional shape) of a uniform inspection pattern in a film thickness direction is measured in a second inspection by an optical measurement method capable of measuring a film thickness of a film.

Therefore, since a measurement value of the film thickness of the uniform pattern measured in the second inspection can be used as a film thickness of the repeat pattern in the first inspection, the number of the fitting parameters of the repeat pattern can be reduced. As a result, regarding the semiconductor device, a three-dimensional shape of the repeat pattern can be measured in a nondestructive and non-contact manner under air pressure with a high throughput and high accuracy in a short time, and the semiconductor device with a shape dimension measured with high accuracy can be obtained.

In addition, the way of layout of the repeat pattern and the uniform pattern can be set based on the characteristics of each production step of a semiconductor to be produced, so that the semiconductor device with a shape dimension measured with higher accuracy can be obtained.

A semiconductor wafer is not particularly limited in the technology presented herein and, for example, includes an elemental semiconductor wafer formed of Si, Ge or the like, a compound semiconductor wafer formed of GaAs, AlAs, GaAlAs, GaN, AlN, or the like, and a SOI wafer in which a Si film is formed on an insulation substrate.

The technology presented herein can be applied to a process for forming concavo-convex objects such as a semiconductor element (such as FET, memory, capacitor, or resistor), a wiring, a wiring trench, an interlayer insulation film, a resist film, and an element isolation trench, on the semiconductor wafer.

That is, according to the technology presented herein, when a film for forming a pattern is deposited and the concavo-convex object serving as the device configuration pattern is formed on the semiconductor wafer, the film for forming the pattern is also deposited and the repeat pattern and the uniform pattern are formed in the first and second inspection regions, and a parameter of the repeat pattern in a repeat direction is measured, and a film thickness of the uniform pattern is measured, whereby a three-dimensional shape of the device configuration pattern can be indirectly measured.

Here, the "film for forming the pattern" means a material film of the concavo-convex object to be formed on the semiconductor wafer, and, for example when a gate electrode of a FET is formed in a device formation region, the material film of the device configuration pattern is composed of a conductive film (such as a polysilicon film), and the repeat pattern and the uniform pattern are composed of the same conductive film (polysilicon film).

According to the technology presented herein, the optical measurement method used in the first inspection includes, as an optical measurement method capable of measuring the three-dimensional pattern shape, the scatterometry method, the AFM method, the CD-SEM method, and the like, but among them, the scatterometry method is preferably used because it can inspect the shape in non-contact and nondestructive manner with a high throughput in a short time, and cut costs for step management. In addition, the optical measurement method used in the second inspection may only have to measure the film thickness of the film, so that the spectroscopic ellipsometry method, a single-wavelength ellipsometry method, an optical interferometry method, and a fluorescent X-ray method may be used, but among them, the spectroscopic ellipsometry method is preferable because it can measure a film thickness with high accuracy with a relatively simple device structure.

Hereinafter, various kinds of the technology presented herein will be described with reference to the drawings.

FIRST EMBODIMENT

Figure 1:
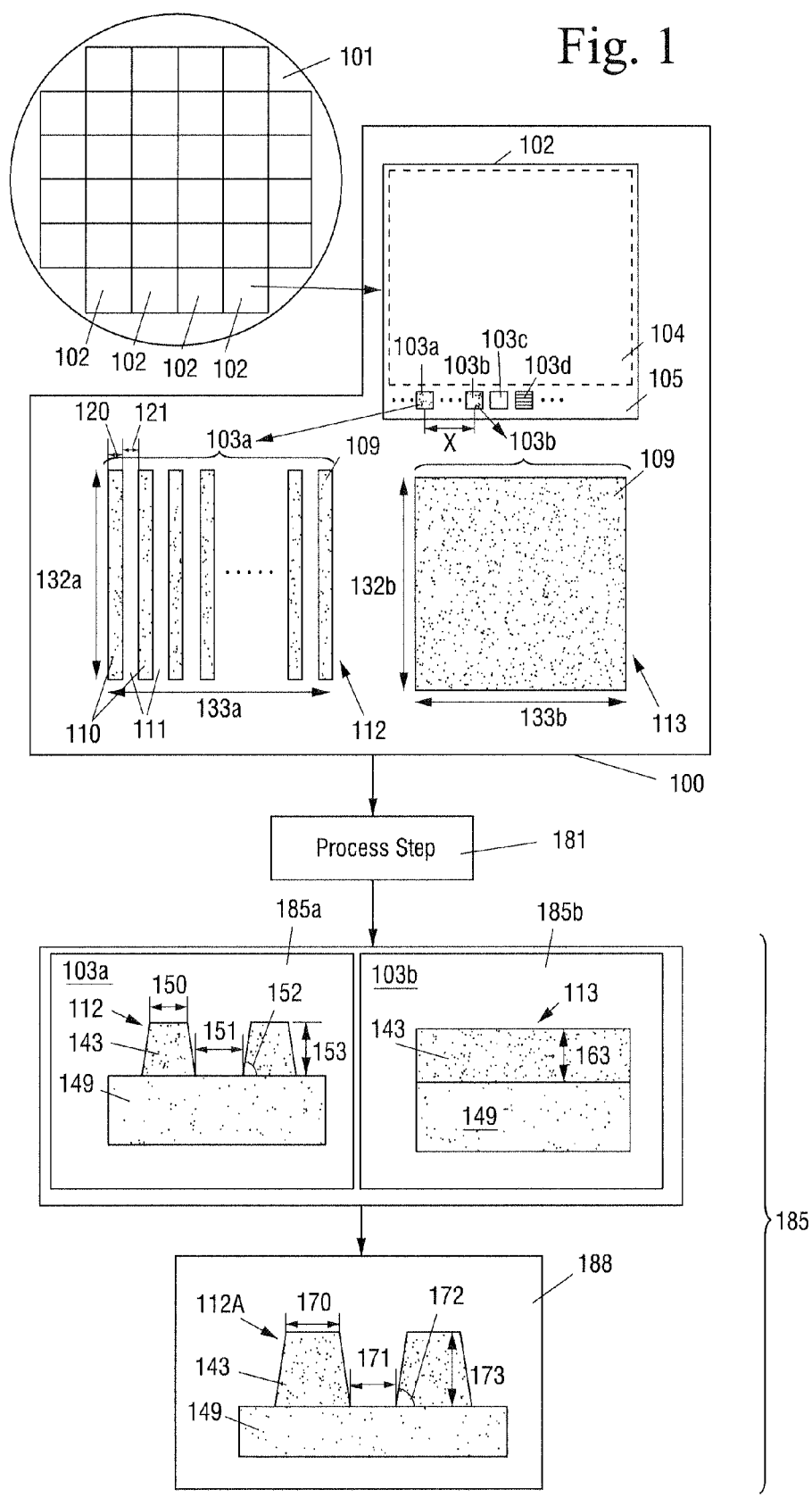
FIG. 1 is a process chart to explain a method for producing a semiconductor device according to a first embodiment of the technology presented herein.

FIG. 1 is a process chart showing a flow of a first embodiment of a method for producing a semiconductor device according to the present invention.

The method for producing the semiconductor device in this first embodiment includes a process step 181, and an inspection step 185, and the inspection step 185 includes a pattern inspection step including a first inspection to measure a parameter of a repeat pattern 112 in a repeat direction in the first inspection region 103a, using an optical measurement method capable of measuring a three-dimensional pattern shape, and a second inspection to measure a parameter of a uniform pattern 113 in a film thickness direction in a second inspection region 103b, using an optical measurement method capable of measuring a film thickness of a film, and a layout data creation step 100 is performed prior to the process step 181.

The first embodiment can be applied to a case where as a device configuration pattern, for example, a gate electrode pattern, an etching stopper film pattern, a wiring pattern, an optical lens pattern, and the like are formed, and a shape dimension of the formed device configuration pattern is measured and managed. The one repeat pattern 112 to be inspected corresponds to one kind of repeat part in the device configuration pattern. Therefore, when the device configuration pattern has several kinds of repeat parts, the several kinds of repeat patterns corresponding to them are formed in a plurality of first inspection regions, respectively.

<Layout Data Creation Step>

The layout data creation step 100 is performed to create layout data 109 containing a layout of a plurality of chip formation regions 102 to be formed on a semiconductor wafer 101, a layout of a device formation region 104 to be formed in the same chip formation region 102, a layout of a plurality of inspection regions 103a, 103b, 103c, 103d, ... to be formed in the same chip formation region 102, a layout of the device configuration pattern to be formed in the device formation region 104, and a layout of an inspection pattern to be formed in each of the inspection regions 103a, 103b, ....

At this time, among the plurality of inspection regions, the inspection pattern of the at least one inspection region 103a is a two-dimensional repeat pattern (so-called line/space (L/S) pattern) 112 alternately provided with lines 110 each having a line width 120 and spaces 111 each having a space width 121, and the inspection pattern of the at least one inspection region 103b is a uniform pattern 113 having no space. In addition, sizes of the inspection regions 103a, 103b, ..., and the line width 120 and the space width 121 in the repeat pattern 112 are set based on the pattern inspection step which will be described below.

In addition, in the first embodiment, the one rectangular device formation region 104 is laid out in the rectangular chip formation region 102, and the inspection regions 103a, 103b, 103c, 103d, ... are laid out in a space 105 which is provided in a place other than the rectangular device formation region 104 in the chip formation region 102 so as to be close to one side of the chip formation region 102. Alternatively, the same device formation regions 104 may be laid out in the one chip formation region 102.

<Process Step>

In the process step 181, based on the above-described layout data 109, the device configuration pattern (not shown) is formed in the device formation region 104, in the chip formation region 102 on a surface of the semiconductor wafer 101, the repeat pattern 112 provided with the identical lines 110 and the identical spaces 111 is formed in the first inspection region 103a, and the uniform pattern 113 having no space is formed in the second inspection region 103b. In addition, in FIG. 1, reference 149 represents a film on which the above-described several kinds of patterns are formed, and this film 149 may be a surface layer of the semiconductor wafer 101, or may be a semiconductor film or an insulation film deposited on the surface of the semiconductor wafer 101.

In the process step 181, a film (insulation film) 143 to form a wiring groove, for example is formed on the semiconductor wafer 101 having a semiconductor element or an element configuration pattern (not shown), and the film 143 is patterned in a photolithography step and a dry etching step, so that the device configuration pattern, the repeat pattern 112, and the uniform pattern 113 can be transferred onto the semiconductor wafer 101.

<Inspection Step>

In the inspection step 185, the pattern inspection step is performed. In this pattern inspection step, with a measurement beam, the first inspection (measurement process 185a) is performed to measure a parameter of the repeat pattern 112 in the repeat direction in the first inspection region 103a, and the second inspection (measurement process 185b) is performed to measure a parameter of the uniform pattern 113 in a film thickness direction in the second inspection region 103b, and then a calculation process is performed. Note that in the present invention, the terms "first" and "second" in the first inspection and the second inspection are used only to be distinguished, and do not means that the inspections are performed first and second in this order.

In the pattern inspection step, first, the measurement process 185b (second inspection) is performed to measure a film thickness 163 of the uniform pattern 113, as the parameter (one-dimensional shape) in the film thickness direction, in the second inspection region 103b having the uniform pattern 113.

In the measurement process 185b to measure the film thickness 163 of the uniform pattern 113, the measurement can be easily made using a general optical film thickness measurement method such as the spectroscopic ellipsometry method. When the above optical method is used, the measurement can be performed in non-contact and nondestructive manner and mostly performed under atmospheric air pressure, so that the method has an advantage of being able to implement a high throughput.

The next measurement process 185a (first inspection) is performed to inspect the parameter (second-dimensional shape) in the repeat direction, in the first inspection region 103a of the repeat pattern 112.

The parameter of the repeat pattern 112 includes a line width 150, a space width 151, a tapered angle 152, and a film thickness 153, for example, but this measurement process 185a is performed to measure the parameters such as the line width 150, the space width 151, and the tapered angle 152 except for the film thickness 153 serving as a parameter in the film thickness direction.

A method for setting the parameters to uniquely express the three-dimensional shape of the repeat pattern 112 may be appropriately set based on the step and structure, while the measurement process 185a is performed only to measure the parameters except for the one-dimensional value in the film thickness direction. Since the one-dimensional parameter in the film thickness direction is removed from the measurement value, the number of parameters required to be measured and fitted can be reduced at the same time, so that accuracy of the measurement value of the measurement process 185a is improved.

The first inspection inspects the first inspection region 103a existing in the same chip formation region 102 as the second inspection region 103b of the uniform pattern 113 which has been measured in the previous second inspection.

Regarding a production step management of the semiconductor device, in many cases, the plurality of chips extracted from the wafer surface are inspected, and their measurement values are used as representative values to know inclination in the surface, but in such a case, it is to be noted that at least one, or preferably all coincide with each other, among the chip formation regions extracted in the second inspection and the chip formation regions extracted in the first inspection. In addition, this also applies to a case where the plurality of semiconductor wafers are unified and managed as one lot, and the wafer extracted from the lot is measured.

Then, using the measurement values of the parameters (the line width 150, the space width 151, the tapered angle 152, and the film thickness 153) in the same chip formation region 102 which have been inspected in the measurement process 185a as described above, measurement values of three-dimensional parameters (a line width 170, a space width 171, a tapered angle 172, and a film thickness 173) in a repeat pattern 112A are obtained in a calculation process 188.

At this time, as for the one-dimensional parameter (film thickness 173) in the film thickness direction, the measurement value of the film thickness 163 is used, and as for the other parameters (the line width 170, the space width 171, and the tapered angle 172), the measurement values of the line width 150, the space width 151, and the tapered angle 152 are used.

Thus, by using the measurement values in the same chip formation region, in the calculation process 188, accuracy can be ensured by using the measurement value of the film thickness 163 of the film 143 in the second inspection region 103b measured in the second inspection, as the film thickness measurement output value 173 of the film 143 in the first inspection region 103a. Furthermore, the line width measurement output value 170, the space width measurement output value 171, the tapered angle measurement output value 172, and the film thickness measurement output value 173 can be outputted as the representative values at the position of the chip formation region, that is, as the values having specific position information.

Figure 2:
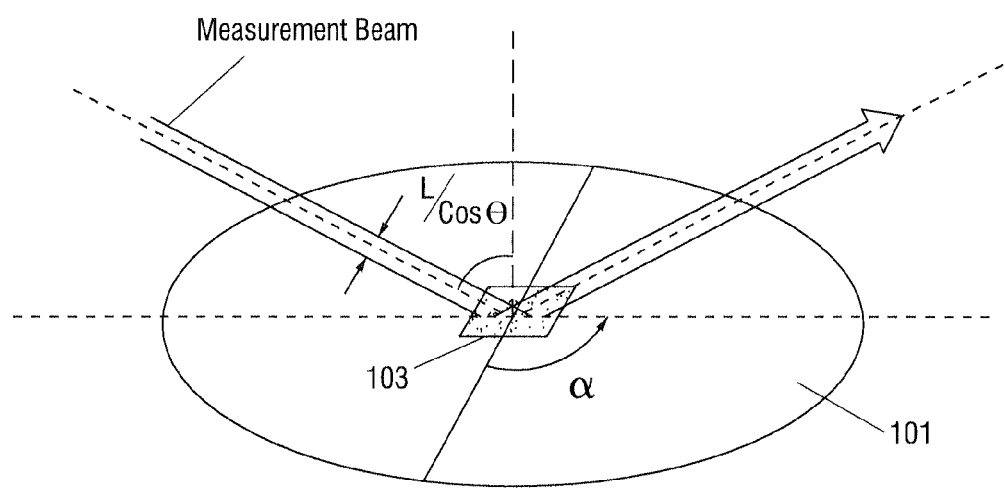
FIG. 2 is a view to explain a pattern inspection step according to the first embodiment.

The first inspection can be performed by the scatterometry method, for example as shown in FIG. 2. In this case also, similar to the second inspection, the measurement can be made in non-contact and nondestructive manner under atmospheric air pressure, so that the measurement can be made with a high throughput. In addition, the inspection regions 103a, 103b, ... shown in FIG. 1 are collectively represented by reference 103 in FIG. 2.

At this time, the fitting is performed using the line width 150, the space width 151, and the tapered angle 152 of the repeat pattern 112, as the parameters. As for the film thickness 153, the fitting is performed, for example, using a fixed value of an expected target film thickness in this step, or using a film thickness value at the same position as in a monitoring wafer which is previously deposited in a deposition device in depositing the film of the uniform pattern 113 as a fixed value.

In the first inspection, since the number of the parameters required to be fitted can be reduced, a high-accuracy measurement value can be obtained.

When the first inspection is performed by the scatterometry method, the measurement beam has a wavelength of 100 nm to 1000 nm, and preferably 200 nm to 800 nm. When the wavelength of the measurement beam is set to 200 nm to 800 nm, the measurement can be performed with high sensitivity and low damage. In addition, in an extreme ultraviolet range of less than 200 nm, a film quality of the measurement target material could be changed due to measurement beam energy, and meanwhile, in an infrared region beyond 800 nm, it is believed that detection sensitivity of the measurement target material is lowered because the wavelength is longer than that of ultraviolet and visible light regions of 200 nm to 800 nm.

Here, when the first inspection is performed by the scatterometry method, it is preferable that in the above-described layout data creation step 100, the size of the inspection region and the line width and the space width of the repeat pattern are set as shown in the following (a) to (e), and in the process step 181, the inspection region having the size and the repeat pattern having the line width and the space width set as shown in (a) to (e) are formed.

(a) A pitch of the L/S pattern constituting the repeat pattern 112, that is, a width of one pattern formed of the one line 110 and the one space 111 in the repeat direction (sum of the line width 120 and the space width 121) is preferably set to be 0.1 to 10 times as long as the wavelength of the measurement beam.

In this case, when the measurement beam is obliquely applied to the inspection region 103 on the semiconductor wafer 101, and the measurement beams are projected from a plurality of angles with respect to an angle cc which is an in-plane rotation direction containing the surface of the semiconductor wafer 101 in the scatterometry method, spectrums of reflected and diffracted light sufficiently change according to the three-dimensional pattern shape of the surface on the semiconductor wafer 101, so that fitting accuracy can be improved (see FIG. 2).

(b) The repeat pattern 112 of the at least one first inspection region 103a of the plurality of inspection regions 103a, 103b, . . . is preferably set to have the line width 120 and the space width 121 which are equal to a minimum pattern density permissible as a layout rule. In this case, a range of value which can be taken as a film thickness value of an actual device laid out according to the layout rule can be known, in a production step having characteristics in which a film thickness varies due to the pattern density.

(c) Each of the inspection regions 103a, 103b, . . . is preferably a square region, 30 square μm or more on one side of 132a, 133a, 132b, 133b, . . . .

Since a long diameter of a standard beam diameter L (see FIG. 2) of the measurement beam on the wafer is about 30 μm in the spectroscopic ellipsometry method and the scatterometry method, the measurement can be made with sufficient reflection light intensity by setting the one side of the inspection region 103 to be 30 μm or more and using the above optical methods in the pattern inspection step.

(d) More preferably, as shown in FIGS. 1 and 2, the long diameter of the beam diameter L on the wafer in the optical inspection method is set as a lower limit value of the one side such as 132a, 133a, 132b, 133b, . . . of the inspection regions 103. This long diameter is about (L/cos θ) wherein θ is an incident angle of the measurement beam with respect to the wafer, so that the one side of each inspection region is preferably set to be longer than (L/cos θ).

(e) A mutual distance between the inspection regions 103a, 103b, . . . is not particularly limited, and it can be about 1 to 10000 μm, for example.

Furthermore, it is preferable that in the first inspection (measurement process 185a), the measurement value (film thickness reference data) of the film thickness 163 of the uniform pattern 113 on the same chip formation region 102, obtained in the previous second inspection (measurement process 185b) is used as the reference for the parameter in the film thickness direction in the repeat pattern 112.

For example, the film thickness data of the film thickness 163 of the uniform pattern 113 on the same chip formation region 102 is stored in a database together with identification information showing a position of the chip formation region 102. Thus, at the time of fitting in the measurement process 185a, the film thickness data of the film thickness 163 in the same chip formation region 102 is used as a reference, and the data is used as the fixed value for the film thickness 153 of the repeat pattern 112, and the fitting is performed for the other parameters (the line width 150, the space width 151, and the tapered angle 152).

In this case, since the fitting is performed using a value which is extremely close to the actual value of the film thickness 153 in the first inspection region 103a, a fitting error caused by an error of the used value is reduced, and accuracy of the measurement value of the first inspection can be improved.

In this case, outputting the measurement value of the line width 150, the space width 151, the tapered angle 152, and the film thickness 153 in the measurement process 185a is equal to outputting the measurements of the line width 170, the space width 171, the tapered angle 172, and the film thickness 173 in the calculation process 188. Therefore, this means that the measurement process 185a is performed also for the calculation process 188.

The semiconductor device according to the first embodiment produced as described above has the device configuration pattern formed in the device formation region 104, and the inspection patterns formed in the plurality of inspection regions 103a, 103b, . . . , on the surface of the semiconductor chip. Thus, regarding this semiconductor device, the inspection patterns have the repeat pattern 112 provided with the identical lines 110 and the identical spaces 111 formed in the first inspection region 103a of the plurality of inspection regions 103a, 103b, . . . , and the uniform pattern 113 having no space, formed in the second inspection region 103b of the plurality of inspection regions.

In this case, it is preferable that each of the inspection regions 103a, 103b, . . . is a square region having one side of 30 μm or more, and the width of the one pattern formed of the one line 110 and the one space 111 in the repeat direction (sum of the line width 120 and the space width 121) of the repeat pattern 112 is 0.1 to 10 times as long as the wavelength of the measurement beam used in the scatterometry method. Furthermore, it is preferable that the repeat pattern 112 of the at least one first inspection region 103a of the plurality of inspection regions 103a, 103b, . . . has the line width 120 and the space width 121 which are equal to the minimum pattern density permissible as the layout rule.

SECOND EMBODIMENT

Figure 3:
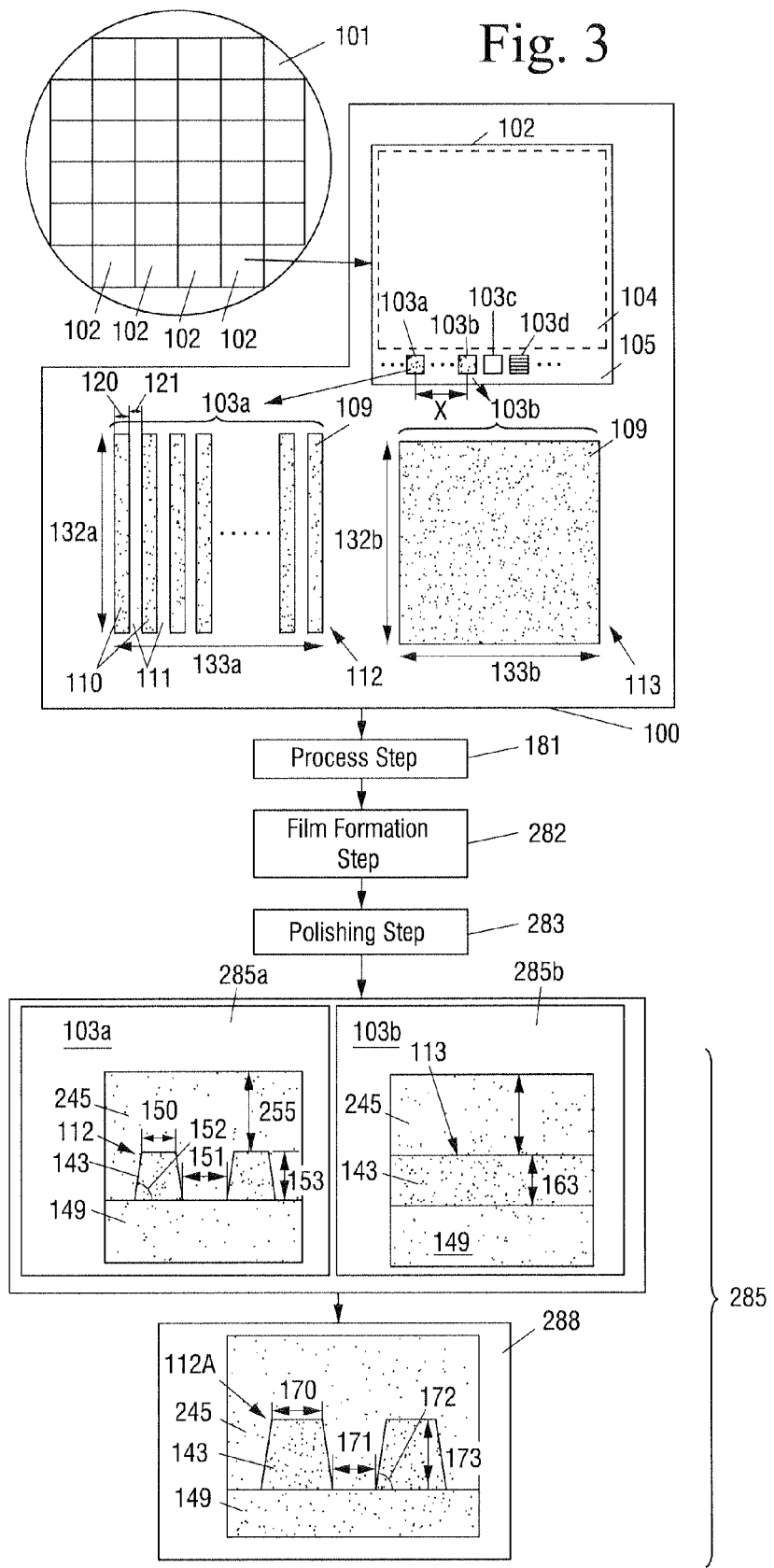
FIG. 3 is process chart to explain a second embodiment of the technology presented herein.

FIG. 3 is a process chart showing a flow of a second embodiment of a method for producing a semiconductor device according to the present invention. In addition, in FIG. 3, the same reference numerals are allocated to the same components as in FIG. 1.

The method for producing the semiconductor device according to this second embodiment includes the layout creation step 100, the process step 181, and an inspection step 285 which are roughly the same as those of the above-described first embodiment, and also includes a film formation step 282 of forming an insulation film 245 at least in the chip formation region 102 on the semiconductor wafer 101, and a polishing step 282 of flattening the insulation film 245 in the chip formation region 102 after the process step 181, and the inspection step 285 includes an insulation film inspection step of measuring a film thickness of the insulation film 245 flattened after the polishing step 283.

That is, according to the second embodiment, after the layout creation step 100 and the process step 181 have been performed in this order similar to the first embodiment, the film formation step 282 of the insulation film 245, the polishing step 283 of the insulation film 245, and the inspection step 285 including the pattern inspection step and the insulation film inspection step are performed in this order.

The second embodiment can be applied to a case where production steps of the semiconductor device include the step of forming the insulation film, and step of flattening the insulation film by polishing. Furthermore, when the inspection region is laid out, according to the process characteristics of the above steps and, especially, according to uniformity in the wafer surface and pattern density dependency, effective accuracy of a one-dimensional shape in the film thickness direction to be used as the reference in measuring a second-dimensional shape of the repeat pattern direction can be improved, and a measurement value of a three-dimensional shape can be obtained with high accuracy.

Hereinafter, a point which is different from the first embodiment will be mainly described in this second embodiment.

<Layout Data Creation Step and Process Step>

It is preferable to make settings as shown in the following (f) to (h) in the layout data creation step 100 in the second embodiment, in addition to the settings of (a) to (e) described in the first embodiment, in view of the process after the film formation step 282 for the insulation film 245.

(f) Each of the sides 132a, 133a, 132b, 133b, of the plurality of inspection regions 103a, 103b, ... is preferably set to be 100 μm or more.

(g) In addition, when it is assumed that a mutual distance X of the plurality of inspection regions 103a, 103b, ... is X μm, an error allowance value due to an in-plane position of fitting parameter used in the first inspection is A nm, and the film thickness of the uniform pattern obtained in the second inspection is Y nm, the mutual distance X is preferably set so as to satisfy the following equation (1);

$$X < 1000 \times A / (Y \times 0.0014) \quad (1)$$

(h) In addition, the mutual distance of the plurality of inspection regions 103a, 103b, ... is preferably set to 3000 μm or less, more preferably to 1000 μm or less, and more preferably to 100 to 300 μm.

In the subsequent process step 181, the plurality of inspection regions are formed with the size and mutual distance, set as described above in the layout data 109 are formed.

<Insulation Film Formation Step>

In the film formation step 282, the inorganic insulation film 245 which is formed of silicon oxide, SiOF, SiOC, porous silica, or the like, can be deposited at least in the chip formation region 102 of the semiconductor wafer 101 by the well-known technique such as CVD, vapor deposition, sputtering to be about 300 to 2000 nm in thickness, for example. This insulation film 245 functions as a wiring interlayer insulation film between a semiconductor element and a lower layer wiring, or for a multilayer wiring.

<Polishing Step>

In the polishing step 283, the insulation film 245 is flattened to form an upper layer wiring structure on the lower layer wiring. This polishing step 283 is performed to polish the surface of the insulation film 245 in the chip formation region 102 so as to reduce surface roughness thereof to 100 nm or less, and, preferably, to 30 nm or less, with an abrasive containing, as abrasive grain, silicon oxide particle, aluminum oxide particle or cerium oxide particle by a CMP method. At this time, it is important to make the film thickness of the insulation film 245 uniform, on the surface of the semiconductor wafer 101.

<Inspection Step>

In the inspection step 285 according to the second embodiment, the pattern inspection step described in the first embodiment and the insulation film inspection step of measuring the film thickness of the insulation film 245 can be performed in parallel.

More specifically, the second inspection (measurement process 285b) is performed first, in the second inspection region 103b, and at this time, a film thickness 265 serving as a parameter of the insulation film 245 flattened in the second inspection region 103b, and the film thickness 163 serving as a parameter of the uniform pattern 113 in the film thickness direction under the insulation film 245 are measured at the same time. However, it is to be noted that each of the insulation film 245 and the uniform pattern 113 need to have translucency with respect to a measurement beam.

Then, similar to the first embodiment, the inspection region 103a having the repeat pattern 112 is measured as the first inspection (measurement process 285a). As the parameters to describe the process shape of the first inspection region 103a, the line width 150, the space width 151, the tapered angle 152, the film thickness 153 of the line 110, and the film thickness 255 of the insulation film 245 are set, for example and the fitting is performed.

At this time, when the line 110 roughly has translucency with respect to the measurement beam (see FIG. 2), similar to the first embodiment, the parameters except for the film thickness 153 which is the one-dimensional value in the film thickness direction are measured. Thus, since the number of parameters required to be measured and fitted can be reduced at the same time, accuracy of the measurement value in the measurement process 285a is improved.

In addition, when the film insulation 143 of the uniform pattern 113 does not have translucency with respect to the measurement beam in the measurement process 285b, the fitting is performed assuming that the film thickness 163 and the film thickness 153 have the same value.

Then, using the measurement values of the parameters (the line width 150, the space width 151, the tapered angle 152, and the film thickness 153) in the same chip formation region 102 which have been inspected in the measurement process 285a as described above, measurement values of the three-dimensional parameters (the line width 170, the space width 171, the tapered angle 172, and the film thickness 173) in the repeat pattern 112A are obtained in a calculation process 288.

At this time, as for the one-dimensional parameter (the film thickness 173) in the film thickness direction, the measurement value of the film thickness 163 is used, and as for the other parameters (the line width 170, the space width 171, and the tapered angle 172), the measurement values of the line width 150, the space width 151, and the tapered angle 152 are used.

As described above, as the measurement values in the same chip formation region are used, in the calculation process 288, accuracy can be ensured by using the measurement value of the film thickness 163 of the film 143 in the second inspection region 103b measured in the second inspection, as the film thickness measurement output value 173 of the film 143 in the first inspection region 103a. Furthermore, the line width measurement output value 170, the space width measurement output value 171, the tapered angle measurement output value 172, and the film thickness measurement output value 173 can be outputted as representative values at the position of the chip formation region, that is, as values having specific position information.

Here, in the second embodiment, the film thickness 265 of the insulation film 245 in the first inspection region 103b, and the film thickness 255 on the line 110 in the insulation film 245 in the first inspection region 103a take values affected by the characteristics of the polishing step due to a difference in layout shape. In this case, the difference in layout shape means that the repeat pattern 112 in the first inspection region 103a is sparsely disposed, while the uniform pattern 113 in the second inspection region 103b is densely disposed. Therefore, pattern flattening performance of the polishing step can be represented by the difference between the film thickness 255 and the film thickness 265 in the same chip formation region 102.

Thus, in the measurement process 285a, the fitting is performed, regarding the film thickness 255 of the insulation film 245 in the repeat pattern 112 not as a simple fixed value but as a variable parameter which is affected by the polishing step.

Therefore, the film thickness data of the film thickness 265 of the insulation film 245 in the same chip formation region 102 obtained in the measurement process 285b is stored in a database together with identification information showing the position of the chip formation region 102, and the film thickness data of the film thickness 265 in the same chip formation region 102 is used as a reference at the time of fitting in the measurement process 285a, and the value is preferably used as an initial value of the fitting for the film thickness 255.

Thus, a fluctuation component corresponding to a film thickness variation of the insulation film 245 caused by a process variation in the wafer surface, between the wafers, and between the lots, between the film formation step 282 and the polishing step 283 can be largely removed from the fitting for the measurement value of the film thickness 255, so that accuracy of the measurement value in the measurement process 185a can be improved. In other words, as for the measurement value of the film thickness 255 of the insulation film 245, in the referred film thickness 265, the fitting may be performed to only the component fluctuating due to the characteristics affected by the layout structure in the polishing process 283 as a variable range of the parameter.

When the fluctuation component corresponding to the film thickness variation of the insulation film 245 is effectively removed from the fitting to the measurement value of the film thickness 255 as described above, the fluctuation component corresponding to the film thickness variation of the insulation film 245 due to the process variation between the wafers and between the lots can be removed by using the data of the same lot and the same wafer. However, it is difficult to completely remove a variation component in the wafer surface due to a difference in set position between the first inspection region 103a and the second inspection region 103b in the same chip formation region 102.

Figure 4:
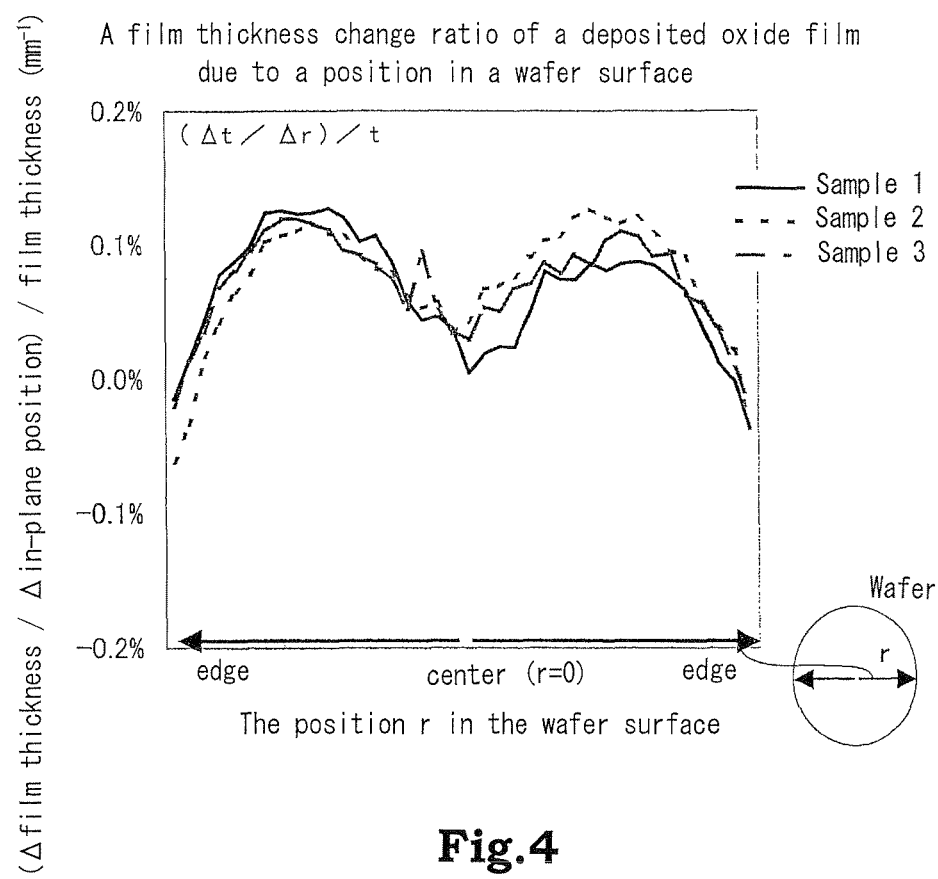
FIG. 4 is a graph showing a film thickness variation of a deposited oxide film due to a position in a wafer surface.

FIG. 4 is a model graph of a film thickness change ratio of a deposited oxide film due to a position in a wafer surface in the film formation step with samples 1 to 3. More specifically, as a typical case where the variation is generated in the wafer surface, the graph shows a case where a silicon oxide film (set film thickness is about 800 nm) is deposited on a semiconductor wafer (diameter is 200 mm) by a HDP-CVD (High Density Plasma Chemical Vapor Deposition) method, with an in-plane deposited film thickness variation such as σ=about 3%.

In FIG. 4, t represents the film thickness of the insulation film 245 in the wafer surface, r represents a position in the wafer surface as a distance from the center of the semiconductor wafer 101, ($\Delta t/\Delta r$) represents a film thickness change amount with respect to the distance r. In addition, in FIG. 4, a horizontal axis shows the position r in the wafer surface (one scale is about 12.5 mm), and a vertical axis shows a ratio ($\Delta t/\Delta r$)/t with respect to the film thickness t. In addition, the position r in the wafer surface is shown by cutting the semiconductor wafer longitudinally along its diameter.

That is, this graph shows a change ratio (%) of the deposited film thickness of the insulation film 245 as the position r in the wafer surface changes, and this value does not depend on the deposited film thickness in general.

In general, since the in-plane variation a in the film formation step is less than 3%, FIG. 4 shows the case where the variation is sufficiently large.

As can be clear from FIG. 4, the change ratio of the film thickness in the case where the in-plane position r is shifted by 1 mm is about less than 0.14% even when the change is largest. Therefore, when an average of the deposited film thickness of the insulation film 245 is about 700 nm, and the in-plane position is within 3 mm or less, the variation component of the film thickness due to the in-plane position is 3 nm or less. That is, with respect to a surface flattening index (100 nm or less of irregularity) of the insulation film 245 in the chip formation region in the polishing step, an error can be about from 3 to less than 10%.

In this respect, the second inspection region 103b and the first inspection region 103a are preferably arranged close to each other within 3000 μm (3 mm) in the chip formation region 102. In this case, the effect of the variation component of the film thickness due to the in-plane position can be reduced to less than 10% as the error at the time of fitting, so that the measurement accuracy can be improved.

In addition, similar to the above, when the second inspection region 103b and the first inspection region 103a are preferably arranged close to each other within 1000 μm (1 mm) in the chip formation region 102, the variation component of the film thickness due to the in-plane position is 3 nm or less even when the average of the deposited film thickness of the insulation film 245 is increased to 2000 nm which is believed to be considerably thick in the normal process, so that the measurement accuracy can be further improved.

As can be clear from the above description, it is further preferable that as for the mutual distance X (μm) between the second inspection region 103b and the first inspection region 103a, when an allowance value of the variation component due to the in-plane position of the fitting parameter is A (nm), and the deposited film thickness of the insulation film 245 formed in the corresponding film formation step is Y (nm), the mutual distance X is set so as to satisfy the following equation (1);

$$X < 1000 \times A/(Y \times 0.0014) \quad (1)$$

and the first and second inspection regions 103a and 103b are laid out.

In addition, as for the above constant value 0.0014, roughly a maximum value of the ratio ($\Delta t/\Delta r$)/t with respect to the film thickness t may be appropriately used.

For example, when the error allowable value A is 3 nm, and the deposited film thickness Y is 700 nm, $$X < 1000 \times 3/(700 \times 0.0014) = 3061 \ \mu m$$

is provided, and it is necessary to set the mutual distance X of the two inspection regions to be less than about 3.061 mm or less, so that X=3 mm is appropriate but X=4 mm is not appropriate.

When a precise measurement needs to be made although it is necessary to deposit a relatively thick film, such that when the deposited film thickness Y is 1200 nm while the error allowable value A is only 1 nm, $$X < 1000 \times 1/(1200 \times 0.0014) = 595 \ \mu m$$

is provided, so that even X=1 is not appropriate, and X=0.5 mm becomes appropriate.

In addition, when the polishing step 283 is performed by the CMP method, as described above, it is preferable that each of the plurality of inspection regions 103a, 103b, . . . is sufficiently as large as 100 square μm or more. That is, it is preferable that the respective one sides 132a, 133a, 132b, 133b . . . of the inspection regions 103a, 103b, . . . are 100 μm or more. In this case, the respective film thicknesses 255 and 265 of the inspection regions 103a, 103b, . . . are not likely to be affected by the layout other than the inspection region, and the relationship between the film thicknesses 255 and 265 is stably determined only by the effect of the layout in each inspection region, so that the value of the film thickness 255 can be surely predicted.

The semiconductor device in the second embodiment produced as described above has the device configuration pattern formed in the device formation region 104, the inspection patterns formed in the plurality of inspection regions 103a, 103b, . . . , and the flattened insulation film 245 covering the device configuration pattern and the inspection pattern, on the surface of the semiconductor chip. In addition, in this semiconductor device, the inspection patterns have the repeat pattern 112 provided with the identical lines 110 and the identical spaces 111 formed in the first inspection region 103a of the plurality of inspection regions 103a, 103b, . . . , and the uniform pattern 113 having no space, formed in the second inspection region 103b of the plurality of inspection regions.

In this case, it is preferable that each of the inspection regions 103a, 103b, . . . is a square region having one side of 100 μm or more, and the width of the one pattern formed of the one line 110 and the one space 111 in the repeat direction (sum of the line width 120 and the space width 121) of the repeat pattern 112, is 0.1 to 10 times as long as the wavelength of the measurement beam used in the scatterometry method. Furthermore, it is preferable that the repeat pattern 112 of at least the first inspection region 103a of the plurality of inspection regions 103a, 103b, . . . has the line width 120 and the space width 121 which are equal to the minimum pattern density permissible as the layout rule. Furthermore, the first inspection region 103a and the second inspection region 103b are preferably arranged within the mutual distance of 3000 μm, and more preferably arranged within 1000 μm.

THIRD EMBODIMENT

Figure 5:
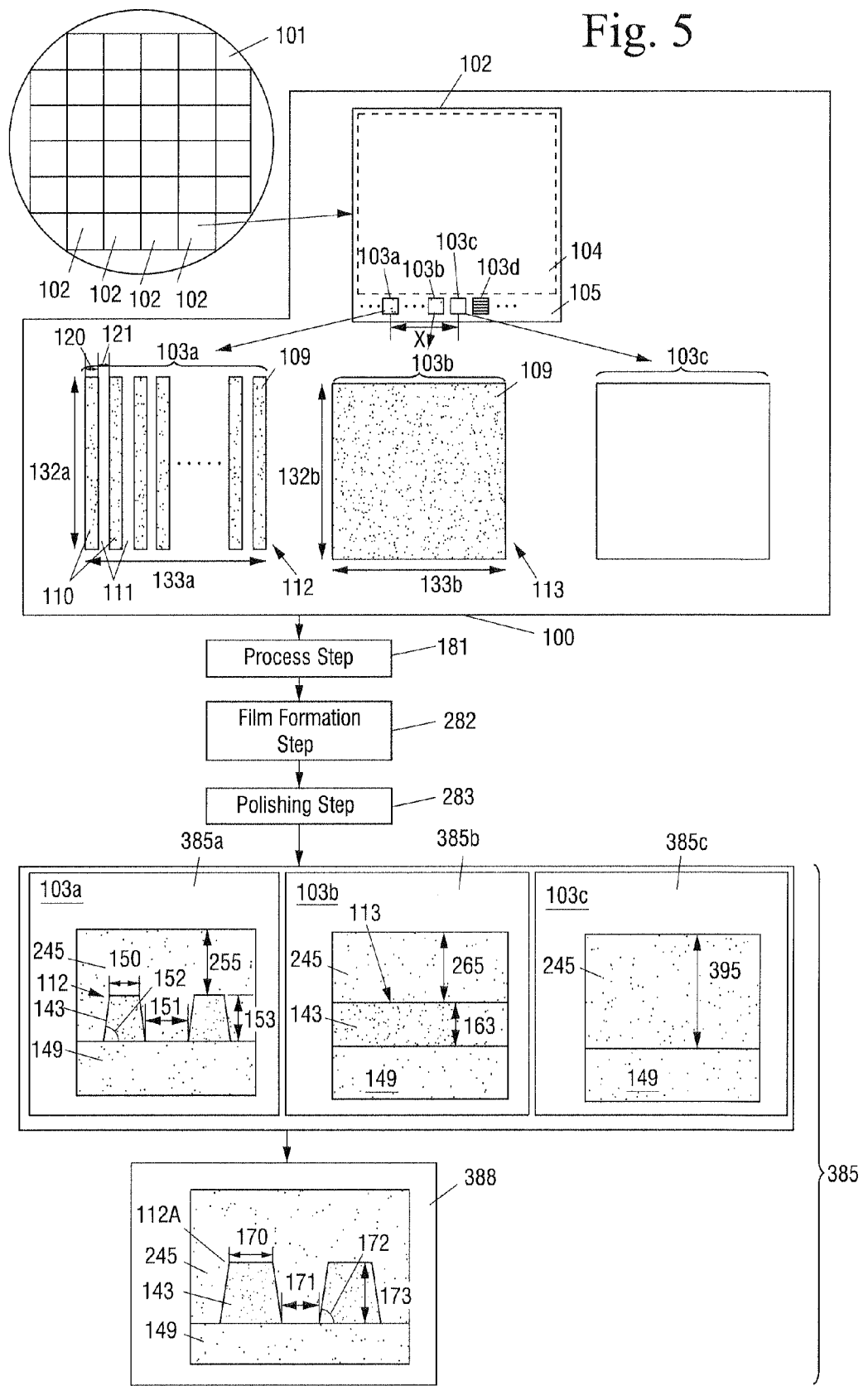
FIG. 5 is a process chart to explain a third embodiment of the technology presented herein.

FIG. 5 is a process chart showing a flow of a third embodiment of a method for producing a semiconductor device according to the present invention. In addition, in FIG. 5, the same reference numerals are allocated to the same components as in FIG. 1.

The method for producing the semiconductor device according to this third embodiment includes the layout creation step 100, the process step 181, and an inspection step 385 which are roughly the same as that of the above-described first embodiment, and also includes the film formation step 282 of forming the insulation film 245 at least in the chip formation region 102 of the semiconductor wafer 101, and the polishing step 283 of flattening the insulation film 245 in the chip formation region 102 after the process step 181.

In addition, the process step 181 includes a step of forming a space pattern having no repeat pattern and no uniform pattern, in the third inspection region 103c of the plurality of inspection regions 103a, 103b, 103c, . . . , and the pattern inspection step further includes a third inspection to measure a parameter of the space pattern in a film thickness direction.

Furthermore, the inspection step 385 includes an insulation film inspection step of measuring a film thickness of the flattened insulation film 245 after the polishing step 283.

Similar to the second embodiment, the third embodiment also can be applied to a case where the production step of the semiconductor device includes the step of forming the insulation film, and the step of flattening the insulation film by polishing. Furthermore, when the inspection region is laid out, based on process characteristics of the steps and, especially, based on uniformity in a wafer surface and pattern density dependency, effective accuracy can be improved in one-dimensional shape in the film thickness direction to be used as a reference in measuring a second-dimensional shape of in a repeat pattern direction, and a measurement value of a three-dimensional shape can be obtained with high accuracy.

Hereinafter, a point which is different from the first embodiment and second embodiment will be mainly described in this third embodiment.

<Layout Data Creation Step to Polishing Step>

In the layout creation step 100 in the third embodiment, the layout data 109 provided with the repeat pattern 112 and the uniform pattern 113, is created in the first inspection region 103a and the second inspection region 103b, respectively of the inspection regions in the semiconductor wafer 101, and also the layout data 109 for forming the space pattern is created in the third inspection region 103c.

In addition, in the layout creation step 100 according to the third embodiment, it is preferable to make settings as described in (a) to (e) in the first embodiment and in (f) to (h) in the second embodiment.

Then, in the process step 181, the plurality of inspection regions 103a, 103b, 103c, . . . are formed with the size and the mutual distance provided based on the layout data 109 set as described above, and in the next film formation step 282, the insulation film 245 is deposited in the chip formation region 102 similar to the second embodiment, and in the next polishing step 283, the insulation film 245 is ground and flattened similar to the second embodiment.

<Inspection Step>

In the inspection step 385, first, as a second inspection (measurement process 385b), the film thickness 265 of the insulation film 245 in the uniform pattern 113 is measured after the polishing step 283 similar to the second embodiment. In addition, according to the third embodiment, as a third inspection (measurement process 385c), a film thickness 395 of the insulation film 245 as the space pattern of the third inspection region 103c in the same chip formation region 102 is measured by the same method as that of the measurement process 285b in the second embodiment.

Then, as a first inspection (measurement process 385a), similar to the first embodiment, the repeat pattern 112 is measured. As parameters to describe the process shape of the first inspection region 103a, for example, the line width 150, the space width 151, the tapered angle 152, the film thickness 153 of the film 143, and the film thickness 255 of the insulation film 245 are set, fitting is performed.

In this third embodiment also, the film thicknesses 255, 265, and 395 in the insulation films 245 in the first to third inspection regions 103a, 103b, and 103c, respectively take values affected by the pattern flattening characteristics of the polishing step, due to a difference in layout shape. When the condition in the polishing step is constant, the pattern flattening characteristics are constant, so that the three film thicknesses 255, 265, and 395 have specific relationships according to the layouts, and the sum of the film thickness 255 and the film thickness 153 takes a value within a range from the film thickness 395 to the sum of the film thickness 265 and the film thickness 163, in general.

By use of the above fact, film thickness data of the film thicknesses 265 and 163 in the second inspection region 103b and film thickness data of the film thickness 395 in the third inspection region 103c in the same chip formation region 102 obtained in the measurement processes 385b and 385c are stored in a database together with identification information showing position of the chips. Thus, when the fitting is performed in the measurement process 385a, the film thickness data of the film thicknesses 265, 163, and 395 in the same chip formation region 102 is used as a reference to limit a variable range of the fitting for the film thickness 255. That is, the sum of the film thickness 255 and the film thickness 153 is limited so as to take a value within a range from the film thickness 395 to the sum of the film thickness 265 and the film thickness 163.

In addition, when the film 143 of the uniform pattern 113 does not have translucency with respect to a measurement beam in the measurement process 385b, the fitting is performed assuming that the film thickness 163 and the film thickness 153 have the same value. This is because an important thing is a difference in relative height among an upper surface of the insulation film 245 in the first inspection region 103a, and an upper surface of the insulation film 245 in the second inspection region 103b, and an upper surface of the insulation film 245 in the third inspection region 103c, and a change amount of the film 143 is considerably smaller than that in most cases, in the third embodiment, similar to the second embodiment.

Thus, since the variable range of the film thickness 255 serving as the fitting parameter in the first inspection region 103a can be limited, the fitting can be performed easily at high speed, so that measurement accuracy can be improved.

Then, using the measurement values of the parameters (the line width 150, the space width 151, the tapered angle 152, and the film thickness 153) in the same chip formation region 102 which have been inspected in the measurement process 385a as described above, measurement values of the three-dimensional parameters (the line width 170, the space width 171, the tapered angle 172, and the film thickness 173) of the repeat pattern 112A are obtained in a calculation process 388.

At this time, as for the one-dimensional parameter (the film thickness 173) in the film thickness direction, the measurement value of the film thickness 163 is used, and as for the other parameters (the line width 170, the space width 171, and the tapered angle 172), the measurement values of the line width 150, the space width 151, and the tapered angle 152 are used, respectively.

Thus, since the measurement values in the same chip formation region are used, in the calculation process 388, accuracy can be ensured by using the measurement value of the film thickness 163 of the insulation film 143 in the second inspection region 103b measured in the second inspection, as the film thickness measurement output value 173 of the insulation film 143 in the first inspection region 103a. Furthermore, the line width measurement output value 170, the space width measurement output value 171, the tapered angle measurement output value 172, and the film thickness measurement output value 173 can be outputted as the representative values at the position of the chip formation region, that is, as the values having the specific position information.

In addition, the third embodiment may be performed as follows.

That is, a test is previously performed similar to the process step, the film formation step, the polishing step, and the inspection step to perform a sample creation step of creating a test sample having a repeat test pattern, a uniform test pattern, and a space test pattern. An inspection step in this sample creation step includes film thickness inspection tests to measure film thicknesses of the repeat test pattern, the uniform test pattern, and the space test pattern.

Thus, in the actual first inspection, using film thickness relationship data regarding the film thickness of the repeat test pattern, the film thickness of the uniform test pattern, and the film thickness of the space test pattern provided in the film thickness inspection tests, and using the film thickness data, the film thickness of the repeat pattern 112 in the first inspection region 103a is calculated and the calculated film thickness of the repeat pattern 112 is used as the parameter.

That is, the several kinds of test samples are previously created, and the relationship (such as film thickness ratio) of the film thicknesses 255, 265, and 395 of the samples is measured by the AFM method or X-SEM method, and the film thickness relationship data is stored in the database. At this time, the film thickness relationship data is defined as a function of pattern densities about the inspection regions 103a, 103b, 103c, . . . contained in the layout data 109. In this case, as the pattern density increases, the film thickness of the insulation film 245 tends to increase in the obtained film thickness relationship data.

Thus, the fitting is performed in the measurement process 385a, by referring to the film thickness relationship data obtained from the test samples, in addition to the film thickness data on the film thicknesses 265 and 395 in the same chip formation region 102. Thus, since the value of the film thickness 255 can be predicted based on the above values, the fitting is further easily performed at high speed, so that the measurement accuracy can be improved.

In addition, when the polishing step 283 is performed by the CMP method, as described above, it is preferable that each of the plurality of inspection regions 103a, 103b, 103c, . . . is sufficiently as large as 100 μm square or more. That is, it is preferable that the respective one sides 132a, 133a, 132b, 133b . . . of the inspection regions 103a, 103b, 103c, . . . is preferably 100 μm or more. In this case, the respective film thicknesses 255, 265, and 395 of the inspection regions 103a, 103b, 103c . . . , respectively are not likely to be affected by the layout except for the inspection regions, and the relationship among the film thicknesses 255, 265, and 395 is stably determined only by the effect of the layout in each inspection region, so that the value of the film thickness 255 can be surely predicted.

Furthermore, when the film thickness relationship information of the film thicknesses 255, 265, and 395 is defined as the function of the pattern densities about the inspection regions 103a, 103b, 103c, . . . contained in the layout data 109, the value of the film thickness 255 which further correctly reflects the CMP process characteristics can be predicted. With this method, even in the region other than the inspection region, in which the relationship of the film thicknesses is measured from the test samples, its film thickness can be predicted based on its pattern density.

The semiconductor device according to the third embodiment produced as described above, is configured similarly to the semiconductor device according to the second embodiment except for the fact that it further has the space pattern formed in the third inspection region 103c.

FOURTH EMBODIMENT

Figure 6:
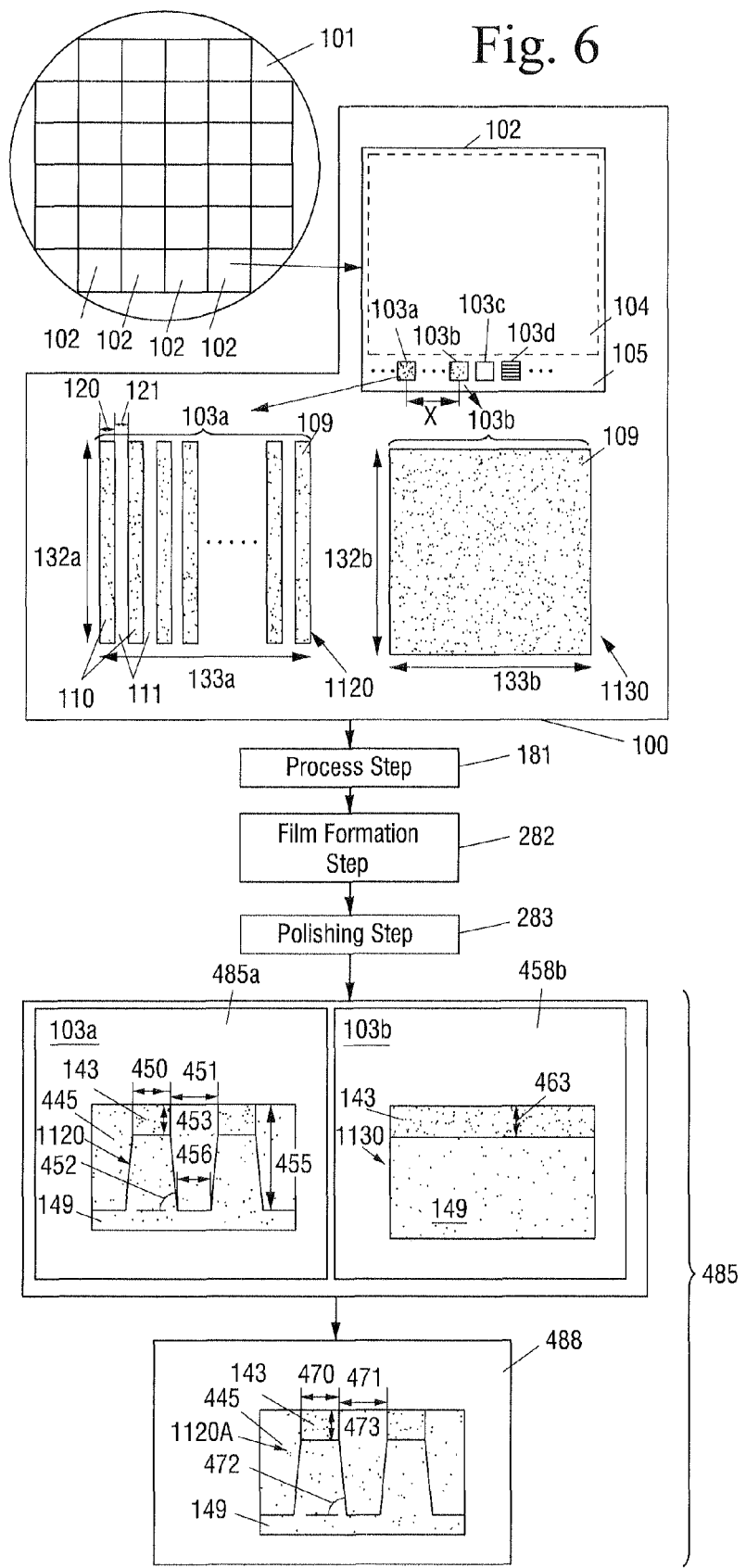
FIG. 6 is a process chart to explain a fourth embodiment of the technology presented herein.
Figure 7:
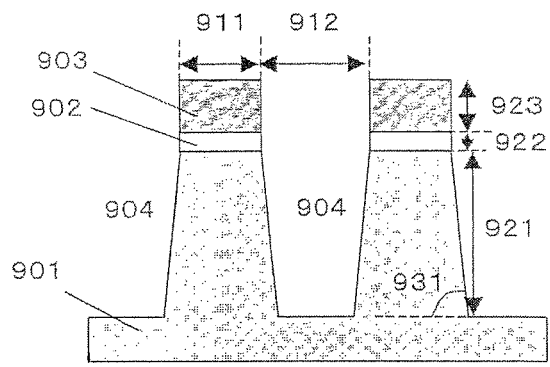
FIG. 7 is a cross-sectional view showing a STI structure in a conventional technique.
Figure 8:
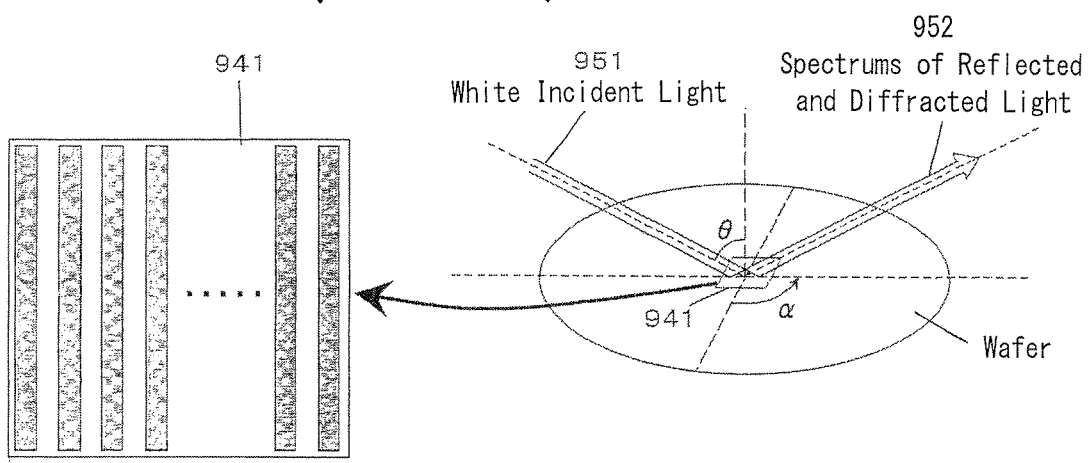
FIG. 8 is a view to explain an application example of an optical scatterometry method in the conventional technique.

FIG. 6 is a process chart showing a flow of a fourth embodiment of a method for producing a semiconductor conductor device according to the present invention. In addition, in FIG. 6, the same reference numerals are allocated to the same components as in FIG. 1.

The method for producing the semiconductor device according to this fourth embodiment includes the layout creation step 100, the process step 181, and an inspection step 485 which are roughly the same as those of the above-described first embodiment, and also includes a film formation step 482 of forming an insulation film 445 at least in the chip formation region 102 of the semiconductor wafer 101, and a polishing step 483 of flattening the insulation film 445 in the chip formation region 102 after the process step 181.

In addition, in the process step 181, a device configuration pattern having a stopper film 143 on its surface is formed in the device formation region on the one surface side of the semiconductor wafer 101, and inspection patterns having the stopper films 143 on their surfaces are formed in the plurality of inspection regions 103a, 103b, . . . , and in the polishing step 483, the insulation film 445 is flattened until the stopper films 143 are exposed on the device formation region and the inspection regions in the chip formation region 102.

Furthermore, the inspection step 485 includes a stopper film inspection step of measuring a film thickness of the stopper film 143 after the polishing step 483.

Similar to the second and third embodiments, the fourth embodiment also can be applied to the case where the production step of the semiconductor device includes the step of forming the insulation film, and step of flattening the insulation film by polishing. Especially it is preferable for formation of the STI structure, and when the inspection region is laid out, based on the process characteristics of the above steps and, especially, based on uniformity in a wafer surface and pattern density dependency, effective accuracy of a one-dimensional shape in the film thickness direction which is used as a reference in measuring a second-dimensional shape in a repeat pattern direction can be improved, and a measurement value of a three-dimensional shape can be obtained with high accuracy.

Hereinafter, a point which is different from the first to third embodiments will be mainly descried in this fourth embodiment.

<Layout Data Creation Step>

Similar to the second embodiment, in the layout creation step 100 according to the fourth embodiment, layout data 109 provided with a repeat pattern 1120 and a uniform pattern 1130, is created in the first inspection region 103a and the second inspection region 103b, respectively among the plurality of inspection regions on the semiconductor wafer 101.

In addition, in the layout creation step 100 according to the fourth embodiment, it is preferable to make settings as described in (a) to (e) in the first embodiment and in (f) and (g) in the second and third embodiments. In addition, according to the fourth embodiment, a mutual distance between the inspection regions is not necessarily 3000 μm or less as described in (f) in the second and third embodiments. This is because the polishing stopper film 143 is provided, so that the effect of the variation in film thickness due to the in-plane position in the film formation step 482 is small in general.

<Process Step>

Then, in the process step 181, the repeat pattern 1120 is formed in the first inspection region 103a, and the uniform pattern 1130 is formed in the second inspection region 103b, based on the layout data 109 set as described above. At this time, the stopper film 143 is formed and patterned on the film 149 on the surface side of the semiconductor wafer 101, and the film 149 is patterned by dry-etching with the stopper film 143 used as a mask, whereby the repeat pattern 1120 is formed in the first inspection region 103a, and the uniform pattern 1130 is formed in the second inspection region 103b.

<Film Formation Step and Polishing Step>

In the next film formation step 482, the insulation film 445 is deposited in the chip formation region 102 similar to the second and third embodiments.

In the next polishing step 483, the insulation film 445 is flattened by the CMP method, for example until the stopper film 143 is exposed. Therefore, the insulation film 445 does not exist on the line 110 of the repeat pattern 1120 and the uniform pattern 1130.

<Inspection Step>

The inspection step 485 includes a first film thickness inspection to measure a film thickness of the stopper film 143 in the uniform pattern 1130 in the second inspection region 103b before the polishing step, and a second film thickness inspection to measure a film thickness of the stopper film 143 in the uniform pattern 1130 in the second inspection region 103b after the polishing step, with the measurement beam (see FIG. 2), and accuracy of the polishing step 483 is inspected by referring film thickness data obtained by the first film thickness inspection and the second film thickness inspection.

In addition, while FIG. 6 shows that the inspection step 485 is performed after the polishing step 483, the first film thickness inspection is performed before the polishing step.

In the inspection step 485, similar to the first embodiment, as the second film thickness inspection (measurement process 485b), the film thickness 463 of the stopper film 143 of the uniform pattern 1130 in the second inspection region 103b is measured.

Then, similar to the first embodiment, as the first film thickness inspection (measurement process 485a), the first inspection region 103a having the repeat pattern 1120 is measured. As parameters to describe the process shape of the first inspection region 103a, a line width 450, a space width 451, a tapered angle 452, a space width 456 of an isolation region bottom, a film thickness 453 of the stopper film 143, and a film thickness 455 of the insulation film 445 are set, for example and fitting is performed. At this time, the film thickness 453 of the stopper film 143 is measured by referring to the film thickness 463 of the stopper film 143 in the second inspection region 103b on the same chip formation region 102 obtained in the measurement process 485b, so that measurement accuracy can be improved.

When the polishing step 983 is performed by the CMP method in the fourth embodiment, process accuracy is preferably managed by a polishing amount of the stopper film 143 partially removed by the polishing. Therefore, the measurement processes 485a and 485b are to be performed before and after the polishing step 483 to compare measurement values.

In this way, whether the polishing is insufficient or excessive can be determined by how much the stopper film 143 has changed before and after the polishing.

Then, using the measurement values of the parameters (the line width 450, the space width 451, the tapered angle 452, and the film thickness 453) in the same chip formation region 102 which have been inspected in the measurement process 485a as described above, measurement values of the three-dimensional parameters (a line width measurement output value 470, a space width measurement output value 471, a tapered angle measurement output value 472, and a film thickness measurement output value 473) of a repeat pattern 1120A are obtained in a calculation process 488.

At this time, as for the one-dimensional parameter (the film thickness measurement output value 453) in the film thickness direction, the measurement value of the film thickness 463 is used, and as for the other parameters (the line width measurement output value 470, the space width measurement output value 471, and the tapered angle measurement output value 472), the measurement values of the line width 450, the space width 451, and the tapered angle 452 are used, respectively.

Thus, when the measurement values in the same chip formation region are used, in the calculation process 488, accuracy can be ensured by using the measurement value of the film thickness 463 of the film 143 in the second inspection region 103b measured in the second inspection, as the film thickness measurement output value 473 of the film 143 in the first inspection region 103a. Furthermore, the line width measurement output value 470, the space width measurement output value 471, the tapered angle measurement output value 472, and the film thickness measurement output value 473 can be outputted as the representative values at the position of the chip formation region, that is, the values having the specific positional information.

In addition, the fourth embodiment may be performed as follows.

That is, a test is previously performed similar to the process step, the film formation step, the polishing step, and the inspection step to further perform a sample creation step of creating test samples having a repeat test pattern and a uniform test pattern. An inspection step in this sample creation step includes a first film thickness inspection test to measure the film thicknesses of the stopper films in the first inspection region and the second inspection region before the polishing step, and a second film thickness inspection test to measure the film thicknesses of the stopper films in the first inspection region and the second inspection region after the polishing step.

Thus, the actual first inspection (measurement process 485a) is performed after the polishing step, and at this time, based on film thickness change relationship data regarding a difference between the film thickness at the time of the first film thickness inspection test and the film thickness at the time of the second film thickness inspection test of the stopper film 143 on the repeat test pattern 1120, and regarding a difference between the film thickness at the time of the first film thickness inspection test and the film thickness at the time of the second film thickness inspection test of the stopper film 143 on the uniform test pattern 1130, and film thickness change amount data regarding a difference between the film thickness at the time of the first film thickness inspection test and the film thickness at the time of the second film thickness inspection test in the uniform pattern 1130, the film thickness of the repeat pattern 1120 in the first inspection region 103a is calculated.

That is, the several kinds of test samples are previously created, and changes of the film thicknesses 463 and 453 of the stopper film 143 before polishing and after polishing are measured with respect to each sample by the AFM method and X-SEM method, and the film thickness change relationship data is stored in the database. At this time, the film thickness change relationship data is defined as a function of a pattern density about the inspection regions 103a and 103b contained in the layout data 109.

Thus, at the time of fitting in the measurement process 485a, the film thickness change relationship data obtained from the test samples is used as a reference, in addition to the film thickness change amount data. Thus, since the value of the film thickness 455 can be predicted based on the above value, the fitting is further easily performed at high speed, so that the measurement accuracy can be improved.

Thus, according to the fourth embodiment, the relationship of the polishing amount of the film thicknesses 463 and 453 in the polishing step 483 may be used as the one corresponding to the relationship of the film thicknesses 255, 265, and 395 (see FIG. 5) in the third embodiment.

Furthermore, according to the fourth embodiment, it is preferable that the repeat pattern 1120 of at least one first inspection region 103a among the plurality of first inspection regions 103a has the same line width 450 and space width 451 which are equal to a minimum pattern density permissible as the layout rule. Thus, since the polishing amount of the stopper film 143 in the whole region in an effective area can be within a range from the polishing amount in the first inspection region 103a to the polishing amount of the second inspection region 103b, the process accuracy can be ensured in the whole effective chip region.

The semiconductor device produced as described above in the fourth embodiment is configured similarly to the semiconductor device in the second embodiment except that a trench serving as an isolation region is formed in the film 149, the repeat pattern 1120 of at least one first inspection region 103a of the plurality of first inspection regions 103a has the line width 470 and space width 471 which are equal to the minimum pattern density permissible as the layout rule, and the stopper film 143 is formed on the pattern.

EXPLANATION OF REFERENCES

100 Layout data creation step
101 Semiconductor wafer
102 Chip formation region
103a First inspection region
103b Second inspection region
103c Third inspection region.
104 Device formation region
109 Layout data
110 Line
111 Space
112, 1120 Repeat pattern
113, 1130 Uniform pattern
120, 150 Line width
121, 151 Space width
143 Insulation film
149 Film
152 Tapered angle
153, 163 Film thickness
170 Line width measurement output value
171 Space width measurement output value
172 Tapered angle measurement output value
173 Film thickness measurement output value
181 Process step (transfer, working process)
185, 285, 385, 485, Inspection step
185a, 185b, 285a, 285b, 385a, 385b, 385c, 485a, 485b Measurement process
188, 288, 388, 488 Calculation process
282, 482 Film formation step
283, 483 Polishing step
L Measurement incident beam diameter
α Rotation angle on wafer of measurement beam incident surface
θ Measurement beam incident angle

The invention claimed is:
1. A method for producing a semiconductor device comprising a process step of forming a device configuration pattern in a device formation region in a chip formation region on a film side of a semiconductor wafer having a film for forming a pattern, and forming inspection patterns in a plurality of inspection regions in the chip formation region, and an inspection step, wherein the inspection patterns have a repeat pattern having identical lines and identical spaces formed in a first inspection region in the plurality of inspection regions, and a uniform pattern having no space, formed in a second inspection region in the plurality of inspection regions, the inspection step has at least a pattern inspection step including a first inspection to measure a parameter of the repeat pattern alternately provided with the line and space in a repeat direction in the first inspection region, by using an optical measurement method capable of measuring a three-dimensional pattern shape, and a second inspection to measure a film thickness of the uniform pattern in the second inspection region by using an optical measurement method capable of measuring the film thickness.

2. The method for producing a semiconductor device according to claim 1, further comprising a film formation step of forming an insulation film at least in the chip formation region on the semiconductor wafer, and a polishing step of flattening the insulation film in the chip formation region, after the process step, wherein the inspection step includes an insulation film inspection step of measuring a film thickness of the flattened insulation film after the polishing step.

3. The method for producing a semiconductor device according to claim 1, wherein the process step further includes a step of forming a space pattern having no repeat pattern and no uniform pattern, in a third inspection region in the plurality of inspection regions, the method further comprises a film formation step of forming an insulation film at least in the chip formation region on the semiconductor wafer and a polishing step of flattening the insulation film in the chip formation region, after the process step, and the pattern inspection step further includes a third inspection to measure a parameter of the space pattern in a film thickness direction, and the inspection step includes an insulation film inspection step of measuring a film thickness of the flattened insulation film after the polishing step.

4. The method for producing a semiconductor device according to claim 1, wherein in the process step, a device configuration pattern having a stopper film on its surface is formed in the device formation region on film surface side of the semiconductor wafer, and inspection patterns having stopper films on their surfaces are formed in the plurality of inspection regions, the method further comprises a film formation step of forming an insulation film at least in the chip formation region of the semiconductor wafer, and a polishing step of flattening the insulation film until the stopper films are exposed on the device formation region and the inspection region in the chip formation region after the process step, the inspection step includes a stopper film inspection step of measuring a film thickness of the stopper film.

5. The method for producing a semiconductor device according to claim 1, wherein the parameters in the repeat direction includes a line width and a space width of the repeat pattern, and a tapered angle when a side wall of the repeat pattern is tapered.

6. The method for producing a semiconductor device according to claim 1, wherein the optical measurement method used in the first inspection is a scatterometry method.

7. The method for producing a semiconductor device according to claim 6, wherein a measurement beam having a wavelength of 200 to 800 nm is used in the scatterometry method.

8. The method for producing a semiconductor device according to claim 6, wherein in the repeat pattern, a width of one pattern provided with one line and one space in the repeat direction is 0.1 to 10 times as long as a wavelength of the measurement beam used in the scatterometry method.

9. The method for producing a semiconductor device according to claim 1, wherein the inspection region is a square region having one side of 30 μm or more.

10. The method for producing a semiconductor device according to claim 1, wherein the inspection region is a square region having one side larger than L/cos θ wherein θ represents an incident angle of the measurement beam entering the inspection region, and L represents a beam diameter of the measurement beam.

11. The method for producing a semiconductor device according to claim 1, wherein the first inspection is performed by referring to film thickness data of the uniform pattern in the same chip formation region, obtained in the second inspection.

12. The method for producing a semiconductor device according to claim 3, wherein the first inspection is performed by referring to film thickness data of the uniform pattern obtained in the second inspection, and film thickness data of the space pattern obtained in the third inspection.

13. The method for producing a semiconductor device according to claim 2, wherein the polishing step is performed by a Chemical Mechanical Polishing Method.

14. The method for producing a semiconductor device according to claim 13, wherein the plurality of inspection regions each have one side of 100 μm or more.

15. The method for producing a semiconductor device according to claim 11, wherein a mutual distance X μm between the plurality of inspection regions, an error allowance value A nm due to an in-plane position of a fitting parameter used in the first inspection, and a film thickness Y nm of the uniform pattern obtained in the second inspection satisfy the following equation (1);

$$X < 1000 \times A/(Y \times 0.0014) \qquad (1).$$

16. The method for producing a semiconductor device according to claim 15, wherein the mutual distance between the plurality of inspection regions is 3000 μm or less.

17. The method for producing a semiconductor device according to claim 16, wherein the mutual distance is 1000 μm or less.

18. The method for producing a semiconductor device according to claim 12, further comprising a sample creation step of creating test samples having a repeat test pattern, a uniform test pattern, and a space test pattern by previously performing tests similar to the process step, the film formation step, the polishing step, and the inspection step, wherein an inspection step of the sample creation step includes film thickness inspection tests to measure film thicknesses of the repeat test pattern, the uniform test pattern, and the space test pattern, the first inspection calculates a film thickness of the repeat pattern in the first inspection region, based on film thickness relationship data relating to the film thickness of the repeat test pattern, the film thickness of the uniform test pattern, and the film thickness of the space test pattern at the time of the film thickness inspection tests, and the film thickness data of the uniform pattern, and the film thickness data of the space pattern, and uses the calculated film thickness of the repeat pattern as a parameter.

19. The method for producing a semiconductor device according to claim 18, wherein
the film thickness relationship data is defined as a function of a pattern density for each inspection region contained in layout data.

20. The method for producing a semiconductor device according to claim 4, wherein
the stopper film inspection step includes a first film thickness inspection to measure a film thickness of the stopper film on the uniform pattern in the second inspection region before the polishing step, and a second film thickness inspection to measure a film thickness of the stopper film on the uniform pattern in the second inspection region after the polishing step with a measurement beam, and accuracy of the polishing step is inspected by referring to film thickness data obtained in the first film thickness inspection and the second film thickness inspection.

21. The method for producing a semiconductor device according to claim 1, wherein
the repeat pattern in the first inspection region has the line width and space width equal to a minimum pattern density permissible as a layout rule.

* * * * *